United States Patent [19]

McCaslin

[11] Patent Number: 6,127,599
[45] Date of Patent: *Oct. 3, 2000

[54] POTATO LEAFHOPPER RESISTANT ALFALFA

[76] Inventor: Mark H. McCaslin, N5157 Shady Birch La., West Salem, Wis. 54669

[ * ] Notice: This patent is subject to a terminal disclaimer.

[21] Appl. No.: 09/172,029

[22] Filed: Oct. 14, 1998

Related U.S. Application Data

[63] Continuation-in-part of application No. 08/631,189, Apr. 12, 1996, Pat. No. 5,908,974.

[51] Int. Cl.$^7$ .............................. A01H 1/04; A01H 5/00; A01H 5/10; C12N 5/04
[52] U.S. Cl. ..................... 800/265; 800/260; 800/298; 435/410
[58] Field of Search .................................. 800/298, 302, 800/260, 265; 435/410

[56] References Cited

U.S. PATENT DOCUMENTS 5,908,974   6/1999   McCaslin ................. 800/298

OTHER PUBLICATIONS

Elden et al. Registration of B16–PLH alfalfa germplasm resistant to the potato leafhopper. Crop Science. vol. 29:1577–1578, 1989.

Kehr et al. Registration of N.S. 76 P2PA1 and N.S. 86 alfalfa germplasms resistant to potato leafhopper yellowing. Crop Science. vol. 24:1003–1004, 1984.

Lehman et al. Registration of UC 73 nondormant alfalfa germplasm with resistance to egyptian alfalfa weevil. Crop Science. vol. 32:284, 1992.

Melton et al. Registration of Rincon alfalfa. Crop Science. vol. 19:741, 1979.

Nichols et al. Effect of organic acid pretreatment on the regeneration and development (conversion) of whole plants from callus cultures of alfalfa, *Medicago sativa* L. Plant Science. vol. 79:181–192. Abstract Only, 1991.

*Primary Examiner*—Elizabeth F. McElwain
*Assistant Examiner*—Melissa L. Kimball
*Attorney, Agent, or Firm*—Rothwell, Figg, Ernst & Kurz

[57] ABSTRACT

The present invention relates to an insect resistant alfalfa seed, alfalfa plant, and an alfalfa variety. More specifically, the invention relates to an alfalfa plant having resistance to the insect potato leafhopper. The invention also relates to an increased level of resistance to potato leafhopper and other pests. The invention further relates to the method of crossing alfalfa plants containing the resistance to potato leafhopper to produce insect resistance.

15 Claims, No Drawings

POTATO LEAFHOPPER RESISTANT ALFALFA

CROSS REFERENCE

This application is a continuation-in-part of U.S. patent application, Ser. No. 08/631,189 filed Apr. 12, 1996, now U.S. Pat. No. 5,908,974.

BACKGROUND OF THE INVENTION

The present invention relates to an alfalfa seed, an alfalfa plant, an alfalfa variety, and an alfalfa hybrid which contain resistance to the potato leafhopper insect. The potato leafhopper resistance of the present invention can be incorporated into various alfalfa genetic backgrounds.

Commercial alfalfa breeders have been successful at incorporating certain types of pest resistance into high yielding alfalfa cultivars. Many newer alfalfa varieties combine resistance to several diseases, insects and nematodes. However, host plant resistance has not been available for the important alfalfa insect pests potato leafhopper (*Empoasca fabae*), alfalfa weevil (*Hypera postica*) and the Lygus bug (*Lygus spp*).

The potato leafhopper (PLH) is a major insect pest of alfalfa, *Medicago sativa,* causing significant economic losses for alfalfa producers in the Midwestern, Northeastern and Southeastern United States. This insect feeds primarily on the second and third crop cuttings each season and causes significant losses in forage yield and forage quality. Leafhopper damage is characterized by stunting of the alfalfa plant and a yellowing of the leaves which is also referred to as hopperburn. Yield losses of 40% have been reported resulting from PLH damage. Decreased protein content of the plant is also associated with PLH damage. The potato leafhopper causes more economic damage to alfalfa than any other insect or disease pest in the United States.

Until recently, breeding alfalfa for resistance to the potato leafhopper has concentrated on increased tolerance to yellowing. Although breeding progress has been made in delaying the onset of the foliar yellowing caused by insect feeding, these plant types suffer PLH induced losses in yield and quality that are similar to susceptible check varieties. The development of alfalfa varieties resistant to potato leafhopper damage has not been successful.

Several annual Medicago species have high densities of glandular hairs (GH) on leaves and stems. In various laboratory studies these GH types have shown some tolerance to potato leafhopper and/or alfalfa weevil. Attempts to cross these GH annuals with perennial alfalfa have been unsuccessful. Three perennial Medicago species have some glandular hairs on vegetative plant parts: *M. prostrata, M. glutinosa* and *M. glandulosa.* Purdue University and USDA/Kansas State University independently developed GH germplasms from these "wild" alfalfa relatives. These GH populations were made available to commercial plant breeders in the mid 1980's.

Early evaluations of the Purdue and Kansas State University GH germplasms were very disappointing. These GH germplasms had very poor vigor and were generally poorly adapted to conditions in the Midwest, including susceptibility to virtually all major alfalfa diseases.

The development of PLH resistance in alfalfa would reduce or eliminate the use of chemical pesticides to control these insects on alfalfa and would also lead to increased alfalfa yield and quality and improved environmental safety.

SUMMARY OF THE INVENTION

The present invention relates to an alfalfa plant, an alfalfa seed, an alfalfa variety, an alfalfa hybrid and a method for producing an alfalfa plant.

More specifically, the invention relates to an alfalfa plant having resistance to the potato leafhopper insect.

The present invention also relates to an alfalfa plant having moderate to high resistance to the alfalfa weevil and the Lygus bug.

The present invention further relates to a method of producing the disclosed alfalfa plants and seed by crossing a potato leafhopper resistant plant of the instant invention with another alfalfa plant. The present invention also relates to all generations of succeeding progeny derived from such a cross.

The present invention further relates to an alfalfa plant having a level of resistance to certain insects, including but not limited to potato leafhopper, alfalfa weevil and Lygus bug.

DETAILED DESCRIPTION OF THE INVENTION

In order to provide an understanding of several of the terms used in the specification and claims, the following definitions are provided:

Potato Leafhopper Resistance—a reaction of the alfalfa host plant which enables it to avoid serious damage from potato leafhopper feeding. The resistant plant reaction is to demonstrate normal growth in the presence of high populations of potato leafhoppers, whereas susceptible plants show significant stunting and yellowing in reaction to insect feeding.

Percentage of alfalfa plants having resistance to potato leafhopper—Alfalfa varieties are heterogeneous populations formed by intercrossing a number of alfalfa clones. Pest resistance in alfalfa varieties is commonly measured in standard tests as the percent of plants in the population that express the resistance trait. The National Alfalfa Variety Review Board in accordance with the recommendation of the North American Alfalfa Improvement Conference has adopted a convention that uses percent resistant plants to describe levels of pest resistance. This convention is as follows: (0–5%)=susceptible, (6–15%)=low resistance, (16–30%)=moderate resistance, (31–50%)=resistance, and (>51%)=high resistance. With most pests, economic losses due to pest damage are minimized or eliminated with varieties containing resistance to high resistance. Individual plants can also have varying levels of resistance. The convention used for measuring PLH damage in this application was patterned after standard tests used for measuring damage/resistance to other pests. Individual plants are scored on a (1–5) scale, where 1=no damage evident and 5=severe stunting and yellowing. Plants scored as 1 and 2 are classified as resistant. The average severity index (ASI) of a variety is the average damage score for 100 random plants. The ASI is often used in combination with percent resistance to characterize pest resistance of alfalfa cultivars.

Using this standard convention, an alfalfa variety described as being resistant to PLH has between (31–50%) of the plants in the variety being scored 1 or 2 in a standard test to measure PLH reaction. Individual alfalfa plants or clones (clonal propagules of individual genotypes) with a resistance score of 1 have very high resistance; a score of 3 show moderate resistance; and a score of 5 show no resistance.

Fall Dormancy (FD)—Most alfalfa plants go dormant in the fall in preparation for winter. The onset of dormancy is triggered by a combination of day length and temperature and is genotype dependent. Fall dormancy scores measure the dormancy response of alfalfa genotypes by quantifying how early dormancy is triggered. The standard fall dormancy test requires that plants are cut off in early September with plant height measured in mid October. Early fall dormant types show very little growth after the September clipping, later fall dormant types demonstrate substantial growth. Fall dormancy is measured on a (1–9) scale, where 1=very early fall dormant and 9=non-dormant. The fall dormancy classes (2–4) are winterhardy types typically planted in the Midwest and Northeastern U.S.

Winterhardiness (WH)—Winterhardiness is a measure of the ability of an alfalfa plant to survive the stresses associated with winter. Cold hardiness is a key feature of the winterhardiness trait. There is a general relationship between fall dormancy and winterhardiness, the early fall dormant types (FD2–4) being more winterhardy than the later fall dormant types (FD5–9). The winterhardiness rating used in this patent are derived from the standard test for measuring winter survival. This standard test measures plant survival and spring vigor following a winter stressful enough to substantially injure check varieties.

Regrowth (Rgw) Rate—Alfalfa is cut 3–4 times per year in the Midwest and Northeastern U.S. The rate of regrowth after cutting varies widely by genotype. It is generally accepted that the rate of regrowth after cutting is one of several factors that influences forage yield potential in alfalfa. Regrowth rate is measured by a visual estimation of canopy height about 10 days after cutting. The scoring system used in this patent was a (1–10 scale) with 1=slowest regrowth and 10=fastest regrowth.

1998 NAAIC Standard Test for evaluating PLH Resistance (1998 NAAIC Standard—As used herein, "1998 NAAIC Standard" means a revised system for determining resistance levels (% resistance) to Potato Leafhopper. This 1998 NAAIC Standard was adopted by the North American Alfalfa Improvement Conference (NAAIC) at their August, 1998 annual meeting. This new standard test lowers the expected resistance level of the standard check PLH40 from 40% resistance to 25% resistance (or to 0.625 of the 1996 Standard). The standard test requires that the percent resistance (%R) of a variety be adjusted to the expected resistance level of the resistant check. Therefore a variety characterized as 40%R under the old standard test procedures (1996) is now properly characterized as 25%R under the new 1998 NAAIC Standard (1996 Standard Value×0.625= 1998 Standard Value).

The present invention is a genetic resistance to the potato leafhopper insect. This results in the resistant alfalfa plants staying healthy and showing neither the stunting or yellowing characteristic of PLH damage.

There is no known resistance to potato leafhopper in any commercial alfalfa cultivar, except for the present invention.

Research to identify resistance to PLH dates back over 30 years. Public and private breeders have screened virtually all available adapted alfalfa germplasm, with no success in identifying a source of PLH resistance. In the 1970's USDA researchers identified genotypes with a delayed yellowing response. Commercial breeders have selected for this trait, and several current alfalfa varieties are described as having resistance or tolerance to potato leafhopper yellowing. However, there is no evidence that this trait offers protection to the economic loss caused by insect feeding. The field test results summarized in Table 1 show the first evidence of PLH resistance high enough to fully protect resistant varieties from PLH damage. The PLH resistant genotypes in this test are the subject of this invention.

There is no information in the literature on genetics of the PLH resistance trait and very little on the mechanism for resistance. Since 1992 Forage Genetics has done considerable research in both of these areas to assist in designing a successful breeding program.

Although a detailed genetic analysis of the PLH resistance trait has not been done, the PLH resistance trait is multigenic with 3–4 genes controlling resistance. The Forage Genetics breeding program has achieved successive increases in the level of PLH resistance which suggests the accumulation of multiple genes. The multiple genetic linkages between PLH resistance and various phenotypic traits (i.e., flower color, multifoliolate expression, recovery rate, leaf disease resistance, fall dormancy, etc.) provide additional evidence for multiple PLH resistance genes. The complex inheritance of PLH resistance is also typical of a multigenic trait. The insect resistance trait of the instant invention has been expressed in many different genetic backgrounds of alfalfa.

The PLH resistance trait is largely recessive since outcrossing only very seldom yields a PLH resistant segregant. The glandular hair trait is also largely recessive, but less strongly so. In 1994–95 crosses between PLH resistant plants of the present invention (with high glandular hair density) and glabrous PLH susceptible commercial type plants, resulted in 6% of the progeny having at least a moderate density of glandular hairs and <1% showed resistance to PLH in 1995 nurseries.

The conventional wisdom concerning glandular hairs and potato leafhopper resistance involved a mechanism of entrapment, where PLH larvae would become entangled on the sticky surface of the glandular hairs. This mechanism suggested that the presence of glandular hairs insured resistance to the insect. In the 1986 nursery it was obvious that plants having a very high density of glandular hairs still could be very susceptible to PLH damage. Recent work at Forage Genetics showed that although the presence of glandular hairs is important for PLH resistance in alfalfa, there are other features of the glandular hairs that are also required. It is not just the presence of glandular hairs per se, but the presence of the "right kind" of glandular hairs which confers PLH resistance.

In our laboratory, when PLH adults or larvae are placed in a cage on an alfalfa stem, it is found that both adults and larvae survive and cause damage on susceptible plants. Plants that showed a strong resistance or anti-biosis reaction will cause death of both adults and larvae within a 24 hour period. Plants with an intermediate level of resistance may cause larval death, but allow survival of the adult insects. The application of this novel selection protocol to identify unique alfalfa plants with a strong antibiosis reaction was critical to increasing PLH resistance to a level sufficient to control insect losses under field conditions. Although an exact mechanism of resistance has not been identified, current research suggests that an insecticidal compound in the exudate of some types of glandular hairs may be involved in PLH resistance. The entrapment mechanism described earlier is not supported by observations in these trials.

As used herein, the term "plant includes plant cells, plant protoplasts, plant cells of tissue culture from which alfalfa plants can be regenerated, plant calli, plant clumps, and plant cells that are intact in plants or parts of plants such as pollen, flowers, seeds, leaves, stems, and the like.

Tissue culture of alfalfa is described in Saunders, J. W. and Bingham, E. T., (1971) Production of alfalfa plants from callus tissue, Crop Sci 12:804–808, and incorporated herein by reference.

Development of the potato leafhopper resistance in alfalfa will provide an important means of providing non-pesticide protection to an important forage crop. Use of the resistance imparts protection from ubiquitous potato leafhopper damage and aids in protection from other insect pests. Additionally, the resistance trait is both user and environment friendly by reducing or eliminating the amounts of pesticides necessary to maintain the crop.

EXAMPLES

The following examples are provided to further illustrate the present invention and are not intended to limit the invention beyond the limitations set forth in the appended claims.

Example 1

Background of the Development of Potato Leafhopper Resistance

In 1984 and 1985, crosses were made between elite alfalfa breeding lines and the glandular haired germplasm releases KS108GH5, KS94GH6 and 81IND-2. The KS germplasms were released by USDA/Kansas State University while 81IND-2 was released by Purdue University. $F_1$ populations were screened in the greenhouse for presence of glandular hairs. Selected plants were intercrossed and exposed to a second cycle of selection for glandular hair density with tandem selection for resistance to anthracnose and or Phytophthora root rot. The resultant populations were transplanted into a 10,000 plant nursery at West Salem, Wis. in May, 1986. This nursery was not sprayed to control insects and PLH populations reached damaging levels by early July.

Plants in the nursery were scored for PLH damage. Although most of the plants in the nursery had at least moderate density of glandular hairs, there were no plants in the nursery without some PLH damage. The presence of a high density of glandular hairs did not provide resistance to potato leafhopper. Furthermore, these GH populations were low yielding and winter sensitive. Seven of 10,000 plants, called 6GH clones, were identified with only slight damage. Vegetative cuttings were taken of these plants and the clones were intercrossed in the greenhouse. A 1987 replicated clonal nursery and half-sib progeny test at West Salem confirmed a moderate PLH resistance in only two of the 6GH clones. Potato leafhopper resistant selections from 1987 nurseries came predominately from the half sib families of these two elite 6GH clones.

The breeding program from 1987 to 1993 involved incremental improvements to the GH germplasm by several cycles of PLH selection to concentrate resistance genes and backcrossing to elite germplasm to improve agronomic performance. It was determined that PLH resistance is largely recessive, therefore a modified backcrossing program was primarily used.

PLH resistant selections were crossed to an elite commercial breeding line and then backcrossed to a different PLH resistant source to restore some PLH resistance expression. From the resultant progeny, vigorous PLH resistant segregates were identified in field nurseries and crossed to a new commercial breeding line followed by backcrossing to a PLH resistant source. This pattern was repeated for several generations, often accompanied by selection for improved resistance to the diseases: Phytophthora root rot, anthracnose, bacterial wilt, Verticillium wilt, Fusarium wilt and Aphanomyces root rot.

Theoretically, the current Forage Genetics (FG) leafhopper resistant populations have approximately 91% of the germplasm tracing to cultivated alfalfa and 9% tracing to the original GH "wild" alfalfa relatives. Alfalfa chromosomes are relatively small allowing limited recombination of genes on short chromosome arms. This allows for blocks of genes (linkage blocks) to be inherited together as a unit. Genetic linkage blocks associated with the PLH resistance genes insure that the wild relatives are contributing more than the theoretical 9%. Although some progress was made in improving vigor and pest resistance, it was discovered that the genes for PLH resistance were linked to several deleterious traits tracing to the original wild parents which limited overall progress in combining PLH resistance and superior agronomic performance. Commercialization of PLH resistance required both increased resistance to the insect and much improved forage yield potential.

Example 2

Development of Commercial PLH Resistant Clones

The final breeding barriers were to break negative genetic linkages to improve yield potential, recovery after cutting, winter hardiness, and leaf disease resistance, while further concentrating PLH resistance. A novel breeding approach achieved this in 1994 and 1995. Beginning in 1992, further backcrossing to cultivated types was suspended and PLH resistant field selections were intercrossed for two generations between PLH resistance selection events which helped break up linkage blocks associated with PLH resistance. The second intercross was followed by screening 10,000–15,000 plants in the field for unique combinations of traits i.e., to identify rare recombination events breaking deleterious linkage arrangements. Unexpectedly, two generations of this recombination/selection protocol enabled us to identify four plants with exceptional PLH resistance, excellent vigor, fast recovery after cutting, good winter hardiness and improved leaf disease resistance. These plants, named HR clones, were used as parents in a series of PLH resistant experimental varieties, synthesized (Syn1) in the greenhouse in December, 1994 and also in the field during the summer of 1995. Limited scale evaluation of the greenhouse produced seed began in the summer of 1995. Larger scale field evaluations, planted from field produced seed, were planted in the fall of 1995. Greenhouse evaluations of these experimentals were carried out from November, 1995 to February, 1996.

Example 3

Methods Used to Assess Levels of Resistance

Alfalfa plants can be evaluated for PLH resistance using either field or laboratory techniques.

The field protocol for evaluating PLH resistance relies on natural PLH populations. Leafhoppers overwinter in the Gulf states and migrate to the Midwest and Northeast on spring wind currents. Populations are commonly above economic thresholds by late June, and remain high until early August. Spaced planted nurseries, grown without insecticide application, are used to evaluate PLH resistance. Susceptible plant rows are included in the nursery as an indicator of damage potential. In early to mid July, after susceptible plant rows are showing severe PLH injury, plants are rated on a (1–5) scale, where 1=no damage evident and 5=severe stunting and yellowing. Plants scored 1 and 2 are classified as resistant. Populations can be characterized for PLH resistance by reporting the percent of resistant plants (percent of class 1 and 2) and average severity index (mean score of 100 random plants). The North American Alfalfa Improvement Conference has adopted definitions for terms characterizing pest resistance in alfalfa. This convention is as follows: susceptible (<5% resistant plants); low resistance (6–15% resistant plants), moderate resistance (16–30% resistant plants), resistant (31–50% resistant plants), and highly resistant (>51% resistant plants).

In 1995 several PLH resistant experimental varieties were evaluated in a field trial for forage yield using two insecticide treatments. One treatment included two spray treatments for each cutting to eliminate leafhopper damage. The second treatment was unsprayed. This design enables the evaluation of yield with and without PLH feeding pressure. A variety with good resistance to PLH will yield similarly in both treatments. The difference in yield between the two treatments for susceptible varieties represents the yield loss due to PLH feeding without host plant resistance.

Example 4

New Genotypes with Resistance to PLH

In 1994 and 1995 four high resistance clones (HR clones) were unexpectedly identified that demonstrated a very high level of resistance to PLH. These were selected from 1994 nurseries. It was determined that experimental varieties synthesized from these, along with other, elite clones demonstrated adequate resistance to prevent economic losses from PLH feeding. In the absence of PLH pressure, these experimental varieties also showed improved yield potential compared to existing commercial alfalfa cultivars in Table 1. Six of these PLH resistant experimentals have been characterized for several other agronomic traits in Table 2.

The value of the four HR clones lies in the unexpected combination of traits expressed in these genotypes. This combination of traits required the breaking of genetic linkages that have plagued the commercialization effort for PLH resistance. This combination of traits, and the method used for selection is described in Example 5.

Example 5

Development of Improved Resistance to PLH

The 1994 nursery was established at Forage Genetics-West Salem, Wis. in May, 1994. Potato leafhopper damage was evident in this nursery starting in late June. Genotypes showing little or no insect damage were identified. Vegetative cuttings of 300 apparently resistant plants were taken in August, 1994. Seed was produced on these 300 plants with greenhouse hand crossing during December, 1994. Half sib progeny of these 300 clones were established in a nursery at West Salem in May, 1995. Notes were taken on PLH resistance in both 1994 and 1995 nurseries during the summer of 1995. There were several of the 300 original clones that showed good resistance in both 1994 and 1995 in the 1994 nursery and had a very high percentage of their progeny showing a PLH resistant reaction in the 1995 nursery. In 1995 there was very severe PLH damage in Wisconsin and most of the Midwest and northeastern U.S. Based on this PLH resistance information and other agronomic traits, 64 of the original clones were tested for antibiosis in a November, 1995 growth chamber study. In this test, five adult leafhoppers were caged on a stem in a no-choice feeding test. Certain of the 64 resistant clones showed a high level of antibiosis, with all five insects dying within the first 12 hours in the cage. Insect survival on susceptible check plants was in excess of 60% for the five day term of the experiment and significant yellowing of the leaves was evident.

In 1994, vegetative vigor and recovery after cutting were evaluated for all "resistant" plants in the 1994 nursery. Plant dry weight was measured to determine improved forage yield for each of four 1995 harvests on the 300 resistant clones in the 1994 nursery. In 1995 the 300 half sib families in the 1995 nursery were also evaluated for vegetative vigor and recovery after cutting.

The 1994 nursery was clipped in late September, 1994 to encourage winter injury. Winter injury and spring vigor notes were taken to determine winterhardiness on all of the original 300 PLH resistant clones in May, 1995. PLH resistant plants in this nursery showed a wide range of winter injury reaction, with approximately 20% of the plants dying over winter, similar to the check cultivar Ranger.

Leaf diseases are common in September and October in West Salem. Leaf disease reaction was scored to determine leaf disease resistance in both 1994 and 1995 nurseries in September, 1995.

Table 3 lists and characterizes four elite HR clones covered in this patent application.

Example 6

Synthesis of PLH Resistant Cultivars

The PLH resistant experimentals, listed in Table 2, each have 10–16 parent clones. The parentage of each experimental variety was unique. Parents were primarily selected based on PLH resistance, forage yield, recovery after cutting, winter hardiness and leaf disease resistance as described in Example 5. All of the listed experimentals have one or more of the four elite HR clones as parents. The remainder of the parentage of these experimentals is composed of other glandular haired plants selected for strength in a particular agronomic trait (e.g. winter hardiness, forage yield, recovery, etc.) combined with at least moderate resistance to PLH. Breeder seed of a particular experimental variety is synthesized by random intercrossing of all parents. Intercrossing can be done by hand in the greenhouse, or in the field using bees as pollinators. The population resulting from the original intercross of the parents is called the first synthetic (Syn1) generation of the variety. The test data on PLH resistant experimentals summarized in Tables 1 and 2 is from this Syn1 generation.

Example 7

Alfalfa Resistance to Other Insects

The Lygus bug is an important economic pest in alfalfa seed production in the western U.S. Most years require multiple insecticide treatments for adequate control of Lygus damage. There has been no report of alfalfa host plant resistance to this insect. In 1995 seed production plots near Nampa, Id., Forage Genetics researchers noted lower Lygus populations on FG potato leafhopper resistant lines. These PLH resistant lines were approximately 1000 yards from a comparable seed production block containing conventional alfalfa germplasm. Other than insecticide treatment, both blocks had identical management. The blocks were sprayed with an insecticide when insect monitoring revealed that Lygus populations exceeded an economic threshold. The conventional germplasm required three insecticide treatments in 1995, the PLH resistant germplasm was sprayed only once. Seed yield at season end was comparable for both blocks.

The alfalfa weevil is a sporadic, but damaging pest in the Midwest and Northeastern U.S. Damage is more severe, and more regular in the Southeast and in the Western U.S. In our Madison, Wis. nursery in 1995, there was light alfalfa weevil feeding, with less apparent on PLH resistant lines when compared to PLH susceptible germplasm.

Example 8

In May, 1995 alfalfa yield trials were established at Forage Genetics at West Salem, Wis. to evaluate the efficacy of PLH resistance in several new Forage Genetics experimental varieties. The experimental design involved two trials, side by side, one of which was sprayed regularly with insecticide to prevent insect damage, the other untreated. The unsprayed trial was host to natural infestation of insect pests, of which the potato leafhopper was by far the most prominent. The same entries, which included a combination of PLH resistant experimentals and leading commercial cultivars, were planted in each trial. Comparing yield of an entry in the Spray (Sp) vs. Non-spray (Ns) treatments, as shown in Table 1, gave an estimate of yield loss due to insect damage, a useful measurement of insect resistance. The Spray treatment consisted of bi-weekly insecticide applications for PLH control while Non-spray had no chemical control.

In 1995, the trials were clipped on June 20 and harvested and weighed on July 28 and September 1. Various Midwestern states reported near record high PLH populations and damage in 1995. Potato leafhopper populations were very high during the entire month of July and moderate in early August. Very significant damage with yellowing and stunting was evident on all susceptible varieties during July. During August, PLH damage on susceptible varieties was moderate. Insect monitoring of the unsprayed plots during June through August did not reveal significant populations of alfalfa insect pests other than PLH. The yield data in Table 1 is the two cut season total expressed in fresh weight (lbs/plot).

The seasonal yield loss due to PLH damage is calculated as the difference between yield in the sprayed and unsprayed treatments, as shown in Table 1. The average yield loss for the listed 1995 PLH resistant experimentals was 5.8%. This compared with a mean yield loss of 27.6% for the commercial check cultivars. Two of the commercial check cultivars, Defiant and Innovator, have been advertised as being tolerant to potato leafhopper yellowing. PLH yield losses for Defiant and Innovator were 21.6% and 28.1% which were slightly less than and equal to the commercial check mean, respectively. This illustrates that tolerance to yellowing is not an effective mechanism for preventing economic losses due to PLH feeding. The 1994 experimental 2L03 represented the highest level of PLH resistance present in the proprietary Forage Genetics breeding program at the time of its synthesis (1994). Although 2L03 yielded higher in the unsprayed trial than did any of the commercial checks, the percent yield loss was equal to the commercial check mean. The level of PLH resistance in 2L03 was insufficient to prevent significant yield loss under high PLH pressure.

The plots in these trials were composed of individual plants, spaced 12 inches apart within twenty five foot rows. This spacing made it possible, in the unsprayed trial, to score individual plants for PLH resistance. As described earlier, plants were scored on a 1 through 5 basis, with 1=no damage through 5=severe yellowing and stunting. Classes 1 and 2 were considered resistant. The results of this scoring are also summarized in Table 1. %R means the percent of alfalfa plants that were resistant to potato leafhopper. ASI means average severity index. This categorization of resistance placed entries into three distinct categories: 1) Resistant and highly resistant which were the 1995 FG glandular haired experimentals; 2) low to moderate resistance which was the proprietary entry 2L03, a 1994 FG glandular haired experimental; and 3) susceptible which were the commercial check cultivars. Differences between these classes were highly significant based on the LSD statistics shown.

The results from this test confirmed efficacy of PLH resistance in this novel germplasm and helped further understanding of what level of resistance is required to provide protection against economic losses caused by PLH feeding. Yield of the new PLH experimentals was competitive with the commercial checks in the insecticide control treatment. The PLH resistance trait in this germplasm had no detrimental effect on yield in the absence of PLH feeding pressure.

TABLE 1

Forage yield of PLH resistant vs. Susceptible alfalfa varieties with and without insect control (1995 test at West Salem, Wisconsin)

| Variety | Forage Yield | | % PLH | PLH | |
|---|---|---|---|---|---|
| | Sp | NSp | Yield Loss | % R | ASI |
| 1995 GH Exp | | | | | |
| 2GO2 | 20.45 | 18.68 | 8.7% | 47.8 | 2.71 |
| 4GO3 | 19.90 | 20.22 | −1.6% | 59.0 | 2.5 |
| 3GO5 | 20.05 | 19.27 | 3.9% | 48.6 | 2.72 |
| 3GO6 | 21.33 | 20.65 | 3.2% | 61.6 | 2.31 |
| 4GO7 | 20.18 | 18.17 | 10.0% | 40.0 | 2.81 |
| 3G10 | 21.28 | 19.02 | 10.6% | 47.3 | 2.70 |
| Mean | 20.53 | 19.34 | 5.8% | 50.7 | 2.63 |
| 1994 GH Exp | | | | | |
| 2LO3 Commercial | 20.68 | 14.93 | 27.8% | 14.7 | 3.75 |
| Defiant | 18.22 | 4.28 | 21.6% | 0.0 | 4.55 |
| DK127 | 18.03 | 12.45 | 30.9% | 0.0 | 4.95 |
| Innovator | 17.63 | 12.67 | 28.1% | 0.0 | 4.81 |
| Magnum IV | 15.53 | 10.77 | 30.7% | 0.0 | 4.99 |
| Ranger | 14.68 | 10.22 | 30.4% | 0.0 | 4.99 |
| WL252 | 15.52 | 11.75 | 24.3% | 0.0 | 4.99 |
| 5454 | 15.70 | 11.38 | 27.5% | 0.0 | 4.95 |
| Mean | 16.47 | 11.93 | 27.6% | 0.0 | 4.89 |
| LSD (.05) | 0.91 | 1.15 | 6.7% | 6.9 | 0.24 |
| C.V. % | 7.2 | 10.8 | 7.3 | 39.2 | 15.0 |

Example 9

The North American Alfalfa Improvement Conference (NAAIC) membership includes virtually every public and private scientist working with alfalfa in the United States. This group has put together standard procedures for evaluating alfalfa varieties for various traits. The procedures outlined in the NAAIC publication "Standard Tests to Characterize Alfalfa cultivars" 1995 update, were used to characterize fall dormancy and disease resistance of several alfalfa varieties as shown in Table 2. Fall dormancy (FD) was measured in October, 1995 in the nursery where 1=most dormant and 9=least dormant. Regrowth (Rgw) was taken in August, 1995 in nursery with PLH chemical control where 10=fastest regrowth and 1=slowest. The categories HR, R, MR, LR and S are abbreviations for high resistance, resistance, moderate resistance, low resistance and susceptible, respectively. Standard test methods for measuring resistance to potato leafhopper are now under development. The six diseases listed: bacterial wilt (Bw), Verticillium wilt (Vw), Fusarium wilt (Fw), anthracnose (An), Phytophthora root rot (Prr) and Aphanomyces root rot (Apn)

are considered to be the most important diseases on alfalfa in the United States.

Table 2 compares the Forage Genetics leafhopper resistant experimentals with several leading commercial check cultivars. The 1995 PLH resistant experimentals 2GO2, 4GO3, 3GO5, 3GO6, 4GO7 and 3G10 have a disease resistance profile competitive with elite commercial cultivars. This multiple pest resistance is a result of several cycles of selection for disease resistance during the development of the PLH resistance germplasm. Fall dormancy and rate of recovery after cutting of the 1995 PLH resistant experimentals is also competitive with the commercial checks. Experimental 2LO3 had a relatively slow recovery. Slow recovery after cutting has been associated with PLH resistance. Linkages between PLH resistance and several deleterious traits were broken in the 1994–95 breeding cycle at Forage Genetics. The 1995 experimentals 2GO2, 4GO3, 3GO5, 3GO6, 4GO7 and 3G10 are the result of this cycle of breeding.

TABLE 2

Characterization of Forage Genetics PLH resistant experimentals

| Variety | FD | Rgw | % R | ASI | PLH Bw | Vw | Fw | Resistance Classification An | Prr | Apn |
|---|---|---|---|---|---|---|---|---|---|---|
| 2GO2 | 2.1 | 7.0 | 47.8 | 2.71 | HR | R | R | HR | HR | R |
| 4GO3 | 2.5 | 7.5 | 59.0 | 2.50 | HR | R | R | HR | HR | R |
| 3GO5 | 2.7 | 7.5 | 48.6 | 2.72 | HR | R | R | HR | HR | R |
| 3GO6 | 2.3 | 7.5 | 61.6 | 2.31 | HR | R | R | HR | HR | MR |
| 4GO7 | 2.8 | 7.5 | 40.0 | 2.81 | HR | R | R | HR | HR | R |
| 3G10 | 2.4 | 7.0 | 47.3 | 2.70 | HR | R | R | HR | HR | MR |
| 2LO3 | 1.8 | 4.5 | 14.7 | 3.75 | HR | MR | R | HR | R | LR |
| Defiant | 2.2 | 7.0 | 0.0 | 4.55 | HR | R | HR | HR | HR | R |
| DK127 | 2.9 | 8.0 | 0.0 | 4.95 | HR | R | HR | HR | HR | R |
| Innovator | 3.0 | 7.5 | 0.0 | 4.81 | HR | R | HR | HR | HR | R |
| Magnum IV | 4.0 | 8.0 | 0.0 | 4.99 | HR | R | HR | HR | R | LR |
| WL252 | 3.1 | 7.0 | 0.0 | 4.99 | HR | R | HR | HR | HR | LR |
| 5454 | 3.9 | 8.0 | 0.0 | 4.97 | HR | R | R | R | R | LR |
| LSD (.05) | 0.45 | 0.54 | 0.91 | 1.15 | | | | | | |
| C.V. % | 10.7 | 5.16 | 7.2 | 10.8 | | | | | | |

Example 10

Commercialization of the PLH resistance trait required two unexpected breakthroughs: 1) concentrating resistance to a level that provides complete protection against economic loss due to PLH feeding, and 2) breaking of linkages between PLH resistance genes and deleterious traits limiting agronomic performance.

Plants with the unique combination of traits to meet these requirements were first identified from our 1994 breeding nursery at West Salem. Four "HR" clones best illustrate this combination of traits. In Table 3 these clones are compared with 2L03 which is a 1994 FG PLH resistant experimental, Defiant which is a contemporary alfalfa cultivar with "tolerance to PLH yellowing", and Ranger which is an older public variety highly susceptible to PLH. The three varieties listed above were represented by 25 random plants for all comparisons.

In Table 3, fall dormancy (FD) was measured in October, 1994 using 1=most dormant through 9=least dormant. Winterhardiness (WH) scores 1–5 were taken May, 1995 where 5=most vigor through 1=dead plant. Regrowth (Rgw) scores 1=10 were taken in June, 1995, where 10=fastest regrowth through 1=slowest. 1994 vigor scores were taken in September, 1994 where 10=best vigor through 1=worst vigor. 1995 yield was a three harvest total expressed as a percent of experimental mean. PLH resistance field ratings were taken in July, 1994 and July, 1995 where 1=no damage through 5=severe stunting and yellowing. PLH lab ratings were taken on November, 1995 where 1=no plant damage/100% insect mortality through 5=severe plant damage.

The 1994 nursery was not treated with an insecticide in 1994 or 1995. PLH damage was evident both years. Genotypic differences in PLH reaction were very significant as evidenced by the 1994 and 1995 field ratings for PLH damage and by 1995 forage yield. PLH resistance for these genotypes was confirmed in the laboratory in "no choice" feeding studies. The four "HR" clones having the resistance of the instant invention received the highest possible resistance rating in each test/observation.

These four clones also demonstrated exceptional yield potential in the field nurseries. Yield and/or vigor were measured both with (harvest 2 and 3, 1995) and without (1994 vigor and harvest 1, 1995) PLH feeding pressure. The "HR" clones show exceptional vigor in all levels of PLH feeding pressure. All of the alfalfa breeding nurseries suffered extensive winter injury during the winter of 1994–95. This provided an excellent opportunity to evaluate PLH resistant genotypes for winter hardiness. The "HR" clones received the highest winterhardiness rating, higher than the mean for Defiant (a very winterhardy commercial check cultivar). The "HR" clones also showed a significantly faster rate of recovery after cutting than the 1994 PLH resistant experimental 2L03.

TABLE 3

Characterization of elite PLH resistant alfalfa clones

| | 1994 Nursery | | | 1994 | 1995 | PLH resistance Field rating | | Lab |
|---|---|---|---|---|---|---|---|---|
| Clone | FD | WH | Rgw | Vigor | Yield | 1994 | 1995 | rating |
| 4gh-708 | 3.0 | 5.0 | 7.5 | 8.0 | 125 | 1.0 | 1.0 | 1.0 |
| 4gh-216 | 3.0 | 5.0 | 7.5 | 8.0 | 129 | 1.0 | 1.0 | 1.0 |
| 4gh-227 | 2.5 | 5.0 | 7.5 | 8.5 | 108 | 1.0 | 1.0 | 1.0 |
| 4gh-497 | 3.0 | 5.0 | 7.5 | 8.5 | 123 | 1.0 | 1.0 | 1.0 |
| 2L03 Mean | 2.0 | 3.0 | 5.5 | 6.5 | 82 | 2.8 | 2.5 | 3.0 |
| Defiant Mean | 2.1 | 3.9 | 7.0 | 7.5 | 80 | 4.3 | 4.0 | 4.3 |
| Ranger Mean | 3.2 | 3.0 | 7.0 | 7.0 | 65 | 5.0 | 4.8 | 5.0 |

Example 11

The alfalfa clone 4gh-708 is a selection for resistance to Phytophthora root rot, bacterial wilt, and Verticillium wilt from FG cross 94-59. 94-59 was the second cycle intercross of 256 plants selected in 1993 from a 1993 Wisconsin nursery for resistance to PLH and improved vigor. 4gh-708 was one of roughly 10,000 plants established in the 1994 PLH nursery at Forage Genetics West Salem, Wis. Evaluation of this clone in 1994 and 1995 revealed a unique and unexpected combination of traits. The clone is characterized for several of these traits in Table 3. The procedures used for this characterization are summarized in Example 10.

Example 12

The alfalfa clone 4gh-216 is a selection for resistance to Phytophthora root rot and bacterial wilt tracing to a half sib family of clone 3GH-128. 3GH-128 was one of 256 plants selected in 1993 from a 1993 Wisconsin nursery for resistance to PLH and improved vigor. 4gh-216 was one of roughly 10,000 plants established in the 1994 PLH nursery at forage Genetics West Salem, Wis. Evaluation of this clone in 1994 and 1995 revealed a unique and unexpected combination of traits. The clone is characterized for several of these traits in Table 3. The procedures used for this characterization are summarized in Example 10.

Example 13

The alfalfa clone 4gh-227 is a selection for resistance to Aphanomyces root rot and bacterial wilt tracing to a half sib family of clone 3GH-36. 3GH-36 was one of 256 plants selected in 1993 from a 1993 Wisconsin nursery for resistance to PLH and improved vigor. 4gh-227 was one of roughly 10,000 plants established in the 1994 PLH nursery at Forage Genetics West Salem, Wis. Evaluation of this clone in 1994 and 1995 revealed an unexpected combination of traits. The clone is characterized for several of these traits in Table 3. The procedures used for this characterization are summarized in Example 10.

Example 14

The alfalfa clone 4gh-497 is a selection for resistance to Phytophthora root rot and bacterial wilt tracing to a half sib family of clone 3GH-130. 3GH-130 was one of 256 plants selected in 1993 from a 1993 Wisconsin nursery for resistance to PLH and improved vigor. 4gh-497 was one of roughly 10,000 plants established in the 1994 PLH nursery at Forage Genetics West Salem, Wis. Evaluation of this clone in 1994 and 1995 revealed an unexpected combination of traits. The clone is characterized for several of these traits in Table 3. The procedures used for this characterization are summarized in Example 10.

Example 15

Revised Procedure for Evaluating PLH Resistance in Alfalfa

The North American Alfalfa Improvement Conference (NAAIC) is responsible for the development and distribution of standard tests for characterizing alfalfa varieties. At their 1996 meeting the NAAIC approved a standard test characterizing PLH resistance, herein called the 1996 Standard. In 1998 a revised test was adopted by the NAAIC (1998 Standards) which adjusted the % resistance values and revised the level of resistance of the standard check (PLH40). The expected level of resistance of the standard check for PLH40 was lowered from 40% to 25%. Thus a variety characterized as 40%R (resistant) under the old standard, is now properly characterized as 25%R under the new 1998 Standard (1996 Standard Value×0.625=1998 Standard Value).

Example 16

Improved PLH Resistance in New Alfalfa Populations

Recurrent phenotypic selection was used to increase levels of pest resistance in alfalfa. The rate of gain from this selection was dependent on the heritability of the trait, the gene frequency of the resistance gene(s) in the population, the effectiveness of the screening process, the effectiveness of the screening process, genetic background of the population being selected, and other factors.

Three cycles of recurrent selection within the alfalfa populations were conducted and resulted in very significant gains in PLH resistance as shown in Table 4. PLH resistance of several populations was evaluated at Madison, Wis. in 1998. This data is summarized in Table 4.

TABLE 4

| Population | 1998 NAAIC Standard % Resistance | 1996 NAAIC Standard % Resistance |
|---|---|---|
| Arrest (4G03) CO | 35 | 56 |
| DK131 (4R25) C1 | 52 | 83 |
| 3A14 C2 | 75 | 120 |
| 4M25 C3 | 86 | 138 |
| PLH40 (R check) | 25 | 40 |
| Ranger (S check) | 0 | 0 |

The data shown in Table 4 illustrates that with recurrent phenotypic selection, levels of PLH resistance were improved over previously described populations. Additional cycles of recurrent selection resulted in potato leafhopper resistance levels approaching 100%.

DEPOSIT INFORMATION

A deposit of the alfalfa seed designated 4M25C3, disclosed above and recited in the appended claims, has been made with the American Type Culture Collection (ATCC), 10801 University Boulevard, Manassas, Va. 20110. The date of deposit was Apr. 17, 2000. The deposit of 2,500 seeds were taken from the same deposit maintained by the inventor since prior to the filing date of this application. All restrictions upon the deposit have been removed, and the deposit is intended to meet all of the requirements of 37 C.F.R. §1.801–1.809. The ATCC accession number is PTA-1702. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A *Medicago sativa* seed containing a genetic resistance to potato leafhopper which is capable of producing a plant with glandular hairs designated 4M25C3 having been deposited under ATCC Accession No. PTA-1702.

2. A *Medicago sativa* plant having glandular hairs, produced by growing the seed of claim 1.

3. Pollen of the plant of claim 2.

4. An ovule of the plant of claim 2.

5. A tissue culture comprising regenerable cells of the plant of claim 2, wherein said plant contains a genetic resistance to potato leafhopper.

6. A method for producing $F_1$ alfalfa seed comprising crossing a first parent alfalfa plant with a second parent alfalfa plant and harvesting the resultant $F_1$ hybrid alfalfa seed, wherein said first or second parent alfalfa plant is the alfalfa plant of claim 2.

7. A first generation ($F_1$) hybrid alfalfa plant produced by growing said hybrid alfalfa seed of claim 6.

8. Viable alfalfa seeds, and plants grown from said seeds, designated 4M25C3 and deposited under ATCC Accession No. PTA-1702 and alfalfa seeds and plants to which the potato leafhopper resistance trait is transferred from said deposited seeds.

9. An alfalfa variety having a percentage of plants resistant to potato leafhopper of greater than 25% using the 1998 NAAIC Standard.

10. An alfalfa variety according to claim 9, wherein said percentage of plants resistant to potato leafhopper is between about 25% and about 35% using the 1998 NAAIC Standard.

11. An alfalfa variety according to claim 9, wherein said percentage of plants resistant to potato leafhopper is between about 36% and about 45% using the 1998 NAAIC Standard.

12. An alfalfa variety according to claim 9, wherein said percentage of plants resistant to potato leafhopper is between about 46% and about 55% using the 1998 NAAIC Standard.

13. An alfalfa variety according to claim 9, wherein said percentage of plants resistant to potato leafhopper is between about 56% and about 65% using the 1998 NAAIC Standard.

14. An alfalfa variety according to claim 9, wherein said percentage of plants resistant to potato leafhopper is between about 66% and about 75% using the 1998 NAAIC Standard.

15. An alfalfa variety according to claim 9, wherein said percentage of plants resistant to potato leafhopper is between about 76% and about 86% using the 1998 NAAIC Standard.

\* \* \* \* \*